United States Patent [19]

Gewartowski

[11] 4,108,914

[45] Aug. 22, 1978

[54] AROMATIC HYDROCARBON ALKYLATION PROCESS

[75] Inventor: Steve A. Gewartowski, Mt. Prospect, Ill.

[73] Assignee: UOP Inc., Des Plaines, Ill.

[21] Appl. No.: 791,619

[22] Filed: Apr. 27, 1977

[51] Int. Cl.$^2$ .............................................. C07C 3/52
[52] U.S. Cl. .................................. 260/671 R; 203/23; 203/80; 203/87; 203/DIG. 8; 260/671 P; 260/674 A
[58] Field of Search ........... 260/671 R, 671 P, 674 A; 203/23, 80, 87, DIG. 8

[56] References Cited

U.S. PATENT DOCUMENTS

| | | | |
|---|---|---|---|
| 3,265,590 | 8/1966 | Redcay | 203/21 |
| 3,437,705 | 8/1969 | Jones | 260/674 A |
| 3,751,504 | 8/1973 | Keown et al. | 260/671 P |

Primary Examiner—Delbert E. Gantz
Assistant Examiner—C. E. Spresser
Attorney, Agent, or Firm—James R. Hoatson, Jr.; John F. Spears, Jr.; William H. Page, II

[57] ABSTRACT

A process for the production of alkylaromatic hydrocarbons by the alkylation of benzene wherein the alkylation zone effluent is fractionated to form a bottoms stream comprising benzene, the alkylaromatic hydrocarbon and a light paraffin. The light paraffin is then removed from the bottoms stream in a first recycle column which produces a recycled overhead stream comprising the paraffin and benzene. The bottoms stream of the first recycle column is separated in a second recycle column, which is operated at about the same bottom temperature but a lower pressure than the first recycle column. The benzene-rich overhead stream of the second recycle column is preferably recycled to the alkylation zone.

6 Claims, 1 Drawing Figure

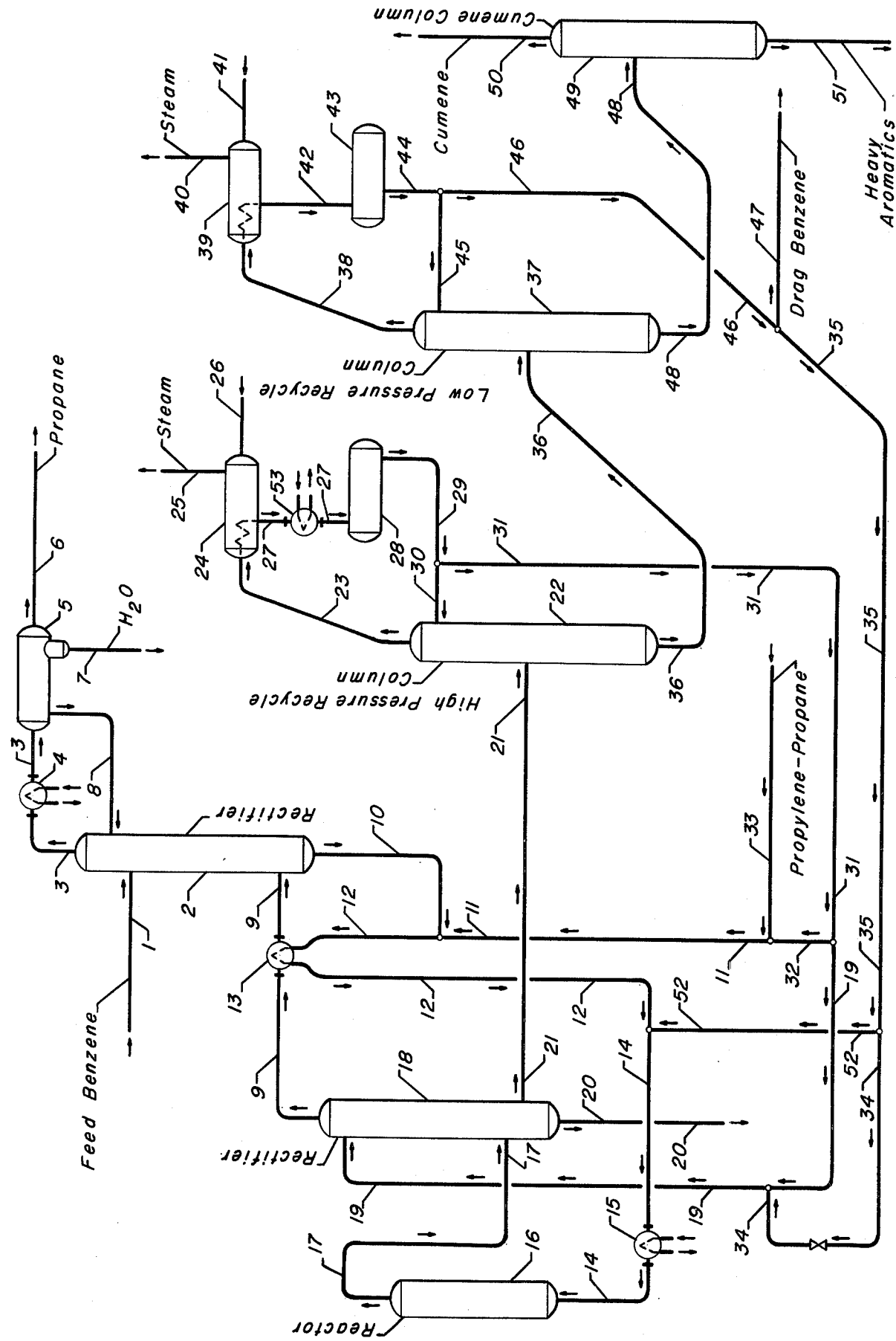

AROMATIC HYDROCARBON ALKYLATION PROCESS

FIELD OF THE INVENTION

The invention relates to a hydrocarbon conversion process. The invention more specifically relates to the alkylation of aromatic hydrocarbons, such as the production of cumene from benzene and propylene, and to fractionation methods by which the effluent of an alkylation zone is separated. The invention therefore relates to processes similar in nature to those found in Classes 260-671 and 203-27.

PRIOR ART

The production of alkylaromatic hydrocarbons by the alkylation of aromatic hydrocarbons is a well established art. One commercial example is the alkylation of benzene with propylene to form cumene, which is often catalyzed by a solid phosphoric acid catalyst. The cumene is then used for the production of phenol, acetone and other chemicals. This particular process and a flow scheme for the separation of the cumene are presented in an article beginning at page 91 of the March, 1971 edition of *Hydrocarbon Processing*.

A particularly pertinent example of the prior art is contained in U.S. Pat. No. 3,510,534 (Cl. 260-671). This reference describes the production of cumene by the alkylation of benzene with propylene derived from a propane-propylene mixture through the use of an SPA catalyst. The effluent of the alkylation zone is passed into a first rectifier or rectification column. Reflux is provided to this column by passing a portion of a recycle benzene stream into the column. The overhead vapors of the first rectifier are heat exchanged against a combined alkylation zone feed stream and passed into a second rectifier. The benzene feed stream is charged to the second rectifier for drying, and the net propane is removed from the process as the overhead of the second rectifier. The bottoms stream of the first rectifier contains benzene and cumene and is passed into a recycle column. The benzene recycle stream is derived from the overhead of this column, and the cumene is withdrawn as the bottoms stream. One portion of the benzene recycle stream is used as reflux for the first rectifier and a second portion is admixed with the feed material to form the combined alkylation zone feed stream. The bottoms stream of the recycle column is directed to a cumene fractionation column for the recovery of the cumene.

The separation of an aromatic hydrocarbon alkylation zone effluent stream comprising cumene through the use of a rectifier and a downstream recycle column is also described in U.S. Pat. Nos. 3,499,826 (Cl. 203—77); 3,520,944 (Cl. 260—671) and 3,520,945.

Heretofore, it has been the practice to utilize a single recycle column and to limit the temperature in the bottom of the recycle column to avoid possible formation of undesirable color bodies in the cumene. The overhead vapor temperature which normally correlates with the temperature limit set on the bottom temperature varies with the pressure used but is normally from about 250° to 300° F. However, it is not possible to recover much usable heat from this overhead vapor since the overhead vapors also contain several percent propane. The presence of this propane makes a lower temperature necessary to condense the benzene in the overhead vapors, and steam generated in the recycle column condenser system is therefore at a temperature well below the temperature of the overhead vapors.

BRIEF SUMMARY OF THE INVENTION

The invention provides a process for the separation of the effluent of an aromatic hydrocarbon alkylation zone in which moderate temperature steam may be produced by the condensation of the overhead vapors of a recycle column producing an aromatic hydrocarbon recycle stream. This is achieved through the use of two recycle columns in series, with the first recycle column removing substantially all of the propane or other light paraffin contained in the bottoms stream of the alkylation zone effluent rectifier. The second recycle column is operated at a lower pressure but with a higher overhead condenser temperature than the first recycle column. This higher condensation temperature allows the production of higher temperature steam. Preferably, the bottom temperature of the first and the second recycle columns are approximately equal to the temperature of the product finishing or rerun column in which the alkylaromatic hydrocarbon is recovered.

DESCRIPTION OF THE DRAWING

The Drawing illustrates the preferred embodiment of the invention. For clarity and simplicity various subsystems and apparatus associated with the operation of the process have not been shown. These items include flow and pressure control valves, pumps, temperature and pressure monitoring systems, reactor and fractionator internals, etc., which may be of customary design. This representation of the preferred embodiment is not intended to preclude from the scope of the invention those other embodiments set out herein or which are the result of reasonable and normal modification of these embodiments.

Referring now to the drawing, a feed stream comprising propylene and propane enters the process through line 33. This feed stream is admixed with a recycle stream comprising benzene which is passing through line 32 to form the material traveling through line 11. This material is admixed with the bottoms stream of a second rectification column, commonly referred to as the second rectifier, from line 10. The resultant stream is carried through heat exchanger 13 by line 12 to the junction with line 52. At this point a second benzene recycle stream is admixed with the hydrocarbons in line 12 to form a combined feed stream carried by line 14. This combined feed stream is heated in means 15 and passed into an alkylation reactor 16. The contacting of the benzene-propylene mixture with an alkylation catalyst maintained at alkylation-promoting conditions effects the reaction of benzene and propylene to form cumene in the reactor.

A reactor effluent stream comprising propane, benzene and cumene is removed in line 17 and passed into a first rectification column 18. This column is refluxed with a portion of a recycle stream comprising benzene and propane which enters through line 19. The overhead vapors of the first rectification column are removed in line 9 and cooled in heat exchange means 13 before passage into the second rectification column 2. Also fed into the second rectification column is the benzene feed stream from line 1. This is done to effect a drying of the benzene feed stream. A resultant overhead vapor stream comprising water and propane is removed in line 3 and passed through a condenser 4. The resultant liquids are decanted in an overhead receiver 5, with water being withdrawn through line 7. Propane is withdrawn through line 8 for reflux to the second rectification column, and a net propane stream is removed in line 6. The flashing operation which is performed as the alkylation zone effluent enters the first rectifier lowers the temperature of this material and causes a very small amount of aqueous phosphoric acid to come out of solution. This material is removed from the bottom of the first rectification column through line 20.

The hydrocarbon bottoms stream of the first rectification column is removed in line 21 and passed into a first or high pressure recycle column 22. The overhead vapor stream of this column comprises propane and benzene. This overhead vapor stream is passed through a steam generator 24 via line 23 to vaporize water entering by line 26 and thereby form a small amount of low pressure steam removed in line 25. The overhead stream is then condensed in cooler 53 and passed into overhead receiver 28 through line 27. The overhead liquid is withdrawn in line 29 and divided between a reflux stream carried by line 30 and the recycle stream carried by line 31. This recycle stream is used in part as reflux for the first rectification column and also to supply a portion of the benzene used to form the combined reactor feed stream. The bottom temperature of the first recycle column 22 is preferably close to that used in the second recycle column 37 and in the cumene finishing column 49.

A net bottoms stream comprising benzene and cumene is removed from the high pressure recycle column 22 and passed into the second or low pressure recycle column 37 through line 36. This bottoms stream is substantially free of propane. An overhead vapor stream of relatively high purity benzene is removed from the low pressure recycle column in line 38 and condensed in a steam generation zone 39. This effects the formation of moderate pressure steam removed in line 40 from the water fed to the process in line 41. The condensed overhead stream is carried by line 42 to an overhead receiver 43. The overhead liquid is removed in line 44 and divided between a reflux stream carried by line 45 and a net overhead liquid stream carried by line 46. A small portion of this stream is removed from the process in line 47 as a drag stream at the rate required to maintain the purity of the recycle benzene. The remainder of the net overhead stream is carried by line 35. Preferably, this material is passed into line 52 and directed to the reactor. Alternatively a portion of this material may be passed through line 34 for use as reflux in the first rectification column. As the overhead vapors of the second recycle column condense at a higher temperature, the resultant overhead liquid is hotter than the corresponding overhead liquid of the first recycle column.

A net bottoms stream comprising cumene is removed from the low pressure recycle column in line 48 and passed into a cumene column 49. The cumene column is operated at a lower pressure than the low pressure recycle column. Using customary conditions, the bottoms stream of the low pressure recycle column is separated into an overhead vapor stream of substantially pure cumene which is removed in line 50, a smaller stream of high boiling contaminants, such as heavy aromatics, is removed in line 51. The heat content of the overhead vapor stream of the cumene column may be used to generate steam in a steam generator not shown in a manner similar to that used on the recycle columns.

DETAILED DESCRIPTION

Large amounts of cumene are manufactured annually for use in the manufacture of phenol and acetone. This is often an integrated process with the cumene and phenol units being interconnected. The cumene is oxidized to form cumene hyperoxide, which is then cleaved to form the phenol and acetone. Phenol production consumes a large amount of low level heat such as supplied by low pressure steam. It is therefore desirable to export a maximum amount of the recoverable heat from the cumene production process to the phenol unit. The largest heat source which was not fully utilized for this purpose in the prior art was the overhead condenser of the benzene recycle column. It is an objective of this invention to provide a process for the production and separation of an alkylaromatic hydrocarbon such as cumene. It is a further objective to provide such a process wherein the condensation of the overhead vapors of a benzene recycle column is performed without the simultaneous condensation of a light paraffin, such as propane, and therefore is performed at a higher temperature than the cited prior art processes.

The subject process may be applied to the alkylation of benzene and other aromatic hydrocarbons, such as toluene, with an acyclic olefin having from two to five carbon atoms per molecule. It is therefore not limited to the production of cumene but may be applied to the production of ethylbenzene, xylene, cymene and propylbenzene. The acyclic olefin may be ethylene, propylene, butylene or an amylene. The production of cumene is, however, the preferred embodiment.

The acyclic olefin is often fed to the alkylation zone in admixture with a paraffin having the same or about the same number of carbon atoms per molecule. There is therefore a net paraffin addition to the process. This paraffin is not reacted in the alkylation zone and must be removed from the process by fractionation of the alkylation zone effluent. This is one function of the fractionation column to which the alkylation zone effluent is charged. A second function of this column in those processes using an SPA catalyst in the alkylation zone is the removal of water from the alkylation zone effluent. This is done to allow control of the water which is contained in the benzene stream which is recycled to the alkylation zone. As known in the art, it is necessary to control the rate at which water enters an SPA alkylation zone to maintain a proper state of catalyst hydration. Based on the combined reactor feed, a water concentration of from about 100 to 500 and preferably from 200 to 250 ppm. is maintained. Operation outside of these ranges normally causes the catalyst to become either dry and powdery or excessively wet and sludge-like.

This first fractionation column, the one to which the alkylation zone effluent is charged, is therefore normally designed to separate the water and most of the unreacted paraffin contained in the alkylation zone effluent into an overhead stream. This overhead stream may be directed into a rectifier as shown in U.S. Pat. No. 3,520,945, into a depropanizer column as shown in U.S. Pat. No. 3,499,826 or into an absorber as taught by U.S. Pat. No. 3,520,944. The bottoms stream of the first column therefore contains those hydrocarbons having boiling points above the water or paraffin. These hydrocarbons are the unreacted benzene or other aromatic hydrocarbon, the product alkylbenzene and various products of side reactions including polymers formed from the olefin and polyalkylated benzenes.

In the subject process a rectification column is used as the first fractionation column. The bottoms liquid of this column therefore also contains a small equilibrium amount of the paraffin. The amount of paraffin in this stream will vary with the identity of the paraffin, the relative concentration of the paraffin and other hydrocarbons in the alkylation zone effluent stream, and the pressure and temperature maintained in the bottom of the rectifier. In the production of cumene the propane concentration in the bottoms stream may vary in the range of about 5–10 mol.%. If the first fractionation column has an adequate stripping section, the use of a second recycle column is not desired.

The bottoms stream of the first fractionation column is passed into a second column commonly referred to as the benzene recycle column because the net overhead product of this column is a benzene-rich stream, much of which is recycled to the alkylation zone. This column has both a rectification section and a stripping section and is therefore reboiled by suitable means. As previously described, the bottom temperature of the benzene recycle column has previously been limited to prevent degradation of the cumene. This has translated into a corresponding maximum temperature for the overhead vapors of about 250°–300° F. Some of the energy of the overhead vapors may be recovered by using this energy to generate steam. Most of the recoverable energy in the overhead vapors is in the heat of vaporization of the various hydrocarbons, and it is necessary to cause their condensation to recover it. Unfortunately, the presence of the relatively volatile paraffin lowers the temperature at which he benzene-rich overhead vapors may be condensed to considerably below the bubble point of pure benzene. The steam which is produced from the condensation of the recycle column overhead vapors has therefore been of a rather low temperature, and a large amount of the heat removed in the overhead system has been wastefully rejected by air or water cooling subsequent to the steam generation.

According to the inventive concept, the paraffin-containing bottoms stream of the first rectifier is passed into a first recycle column operated with a bottom temperature near, but preferably not above, that used in the cumene column. This is a difference from the prior art. The composition of the bottoms stream of the recycle column is regulated by adjustment of the pressure at which the column is operated. Unless otherwise specified, the column pressures set out herein refer to the pressures measured at the top of the column. The first recycle column is maintained at a pressure which produces overhead vapors which are free of the product alkylaromatic hydrocarbon but contain some benzene and essentially all of the unreacted paraffin in the bottoms stream of the first rectifier. In the production of cumene the overhead vapors of the first recycle column will contain about 10–50 mol.% propane. The bottoms stream of the first or high pressure recycle column will be substantially free of the paraffin. As used herein the phrase "substantially free of" a compound is intended to indicate the concentration of the specified compound is less than 1.0 mol.%.

All of the alkylaromatic hydrocarbon product is therefore concentrated in the bottoms stream of the first recycle column and is passed into a second recycle column. This column is preferably operated at about the same bottom temperature as the first recycle column. The second recycle column is therefore also operated with a bottom temperature near, but preferably not above, that used in the cumene column. The bottom temperature of each recycle column is preferably within 50° F of the bottom temperature of the product finishing or rerun column. Unless otherwise specified, all fractionation column temperatures set out herein are intended to refer to the temperature of the liquid phase in the bottom of the column. The pressure in the second recycle column is maintained sufficiently below that in the first recycle column to ensure that the bottoms stream of the second recycle column is substantially free of benzene. The pressure difference between the two columns will preferably be in excess of about 200 psig. The overhead vapors of this column should be rich in benzene, that is contain over 80 mol.% benzene and substantially free of the paraffin. It is therefore totally condensible at a higher temperature than the overhead vapors produced in the prior art single recycle column or in the first recycle column. This allows the production of sizable amounts of steam having a temperature of about 280°–300° F. when a steam generator is used as the overhead condenser. This is a definite advantage over the prior art since there is often a need for sizable amounts of steam in the operations associated with the further processing of the product alkylaromatic hydrocarbon.

The subject process also differs from the prior art in the production and utilization of two recycle streams of different composition and temperature. The colder recycle stream produced by the first recycle column is preferably used as much as possible as reflux for the first rectifier. Its lower temperature is therefore used advantageously. As a corollary to this, the hotter recycle stream produced by the second recycle column is preferably recycled to the alkylation zone. Compared to the prior art this reduces the heat input required to bring the combined feed stream up to the desired alkylation temperature. This is because the prior art produced a single cold recycle stream at the lower condensation temperature. The extra cooling required to condense the benzene which was recycled as part of the reactor feed material therefore had to be replaced in heating the feed stream.

The bottoms stream of the second recycle column is passed into a finishing column operated at relatively low pressure. This column is commonly referred to as the cumene column, and is preferably operated at a pressure of less than 25 psig., and more preferably less than 15 psig. when cumene is being separated as the overhead product. The bottom temperature of this column is preferably maintained in the range of from about 430° to about 480° F. As it is preferred that the recycle columns are operated at a pressure within 50° F. of this range, the preferred recycle columns' bottom temperature is within the range of from about 380° to 480° F. Those skilled in the art of fractionation may determine the pressures which correlate with temperatures within this range to produce bottoms streams of the desired composition. These pressures will vary with the hydrocarbons being separated.

The reaction zone is maintained at alkylation-promoting conditions which include a pressure of about 300 to 1000 psig. and a temperature of about 300° to 600° F. The liquid hourly space velocity of the reactants may range from about 0.5 to 2.5. It is preferred that an excess of the aromatic hydrocarbon be present in the reaction zone. The mole ratio of the aromatic hydrocarbon to the olefin should be within the broad range of 3:1 to 20:1. A ratio of about 8:1 is preferred for the production of cumene. It is preferred that the reactant stream be mixed-phase throughout the reactor. The feed stream therefore preferably contains some unreactive light paraffins having the same number of carbon atoms per molecule as the olefin. A paraffin having a lower, or possibly a higher, number of carbon atoms per molecule may also be used. In the production of cumene it is preferred that the amount of propane in the reaction zone feed stream be at least equal to the amount of propylene in this stream. More specifically, a propane to propylene mole ratio of about 2.0 is acceptable during cumene production. This ratio may be accomplished by using a dilute propylene feed stream or by recycling the propane.

Preferably, the catalyst used in the reaction zone is one commonly referred to as an SPA catalyst. Suitable SPA catalysts are available commercially. As used herein the term "SPA catalyst" or its equivalent is intended to refer generically to a solid catalyst which contains as one of its principal raw ingredients an acid of phosphorus such as ortho-, pyro- or tetra-phosphoric acid. These catalysts are normally formed by mixing the acid with a siliceous solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, fullers earth and iron compounds including iron oxide have been added to the carrier to increase its strength and hardness. The combination of the carrier and the additives normally comprises about 15-30 wt.% of the catalyst, with the remainder being the phosphoric acid. However, the amount of phosphoric acid used in the manufacture of the catalyst may vary from about 8-80 wt.% of the catalyst as described in U.S. Pat. No. 3,402,130. The amount of the additive may be equal to about 3-20 wt.% of the total carrier material. Further details as to the composition and production of typical SPA catalysts may be obtained from U.S. Pat. Nos. 3,050,472; 3,050,473 and 3,132,109 and from other references.

The invention may be further illustrated by this example based on the production of cumene by the alkylation of benzene with propylene. For clarity, reference will be made to lines and vessels shown in the Drawing. The feed to the reaction zone is derived in part from the bottoms stream of the second rectifier 2 which comprises about 1,293 mph (moles per hour) of propane and 3,294 mph of benzene and various other hydrocarbons. The propylene-propane feed stream from line 33 enters the process at the total rate of about 852 mph. The combined feed stream has a flow rate of about 9,196 mph, of which approximately 6,275 mph is benzene and about 1,561 mph is propane. It is split into two identical streams, each of which is passed into the bottom of a reactor at a pressure of about 550 psig. and a temperature of about 380° F. The catalyst used is a standard SPA catalyst.

The mixed-phase effluents of the two reactors are cooled from about 437° F. to about 394° F. by being flashed into the first rectifier 18. The total reactor effluent has a flow rate of about 8,418 mph. Also fed to the first rectifier is a 600 mph benzene-rich reflux stream from line 19. The first rectifier is operated with a bottom temperature of about 394° F. at a 270 psig. top pressure. The overhead vapor stream is removed in line 9 at a temperature of about 379° F. and cooled to about 310° F. in heat exchanger 13 before being passed into the second rectifier. The first rectifier contains eight fractionation trays and the second rectifier contains 20 fractionation trays.

The benzene feed stream in line 1 enters the second rectifier at the rate of about 741 mph at a temperature of approximately 80° F. The overhead vapor of this column has a temperature of about 123° F. and is cooled to near 100° F. in the overhead condenser. The overhead receiver is maintained at a pressure of approximately 250 psig. About 7 mph of water and 68 mph of vaporous hydrocarbons are removed from the receiver. This net overhead vapor is mainly propane. A stabbed-in reboiler is utilized to maintain a bottom temperature of about 251° F.

The net hydrocarbon bottoms stream of the first rectifier is removed in line 21 at a temperature of approximately 394° F. and passed into the first recycle column 22 by a pump not shown. This column is operated with a bottom temperature of about 480° F. and a bottom pressure of approximately 385 psig. and therefore higher in the pressure than the first rectifier. The overhead vapors removed in line 23 have a temperature of about 420° F. These vapors are used to produce 280° F. steam in a steam generator and then condensed in a cooler. The net overhead liquid removed in line 31 has a flow rate of approximately 1,518 mph and contains over 14 mol.% propane and a large concentration of benzene. The bottoms stream removed from the first recycle column is substantially free of propane and is passed into the second recycle column. This second recycle column is operated with a bottom temperature of about 480° F., but with a lower overhead pressure of approximately 77 psig. The overhead vapors have a temperature of about 315° F., and are used to produce 280° F. steam in a steam generator. They are totally condensible at a temperature of about 280° F. The net overhead removed in line 46 has a flow rate of about 2,531 mph, of which about 2,305 mph is benzene. This overhead stream also contains some cumene and non-aromatic hydrocarbons having boiling points above propane. The drag stream in line 47 is about 14 mph.

A bottoms stream of about 750 mph is passed into the cumene column via line 48. This third column is operated with a bottom temperature near 480° F. and an overhead temperature of about 374° F. The overhead vapor stream has a pressure of about 20 psig. and is cooled to approximately 360° F. in a steam generator used as an overhead condenser. The net overhead product is a 716 mph stream of high purity cumene. A bottoms stream of impurities having a flow rate of about 34 mph is removed in line 51. The advantage of the subject method is apparent from the fact that it allows the recovery of an additional 50 million BTU/hr. in the form of 280° F., 34 psig. steam as compared to a similar process having the same heat inputs but utilizing only one recycle column.

I claim as my invention:

1. In the process for the production of alkylaromatic hydrocarbons by the alkylation of benzene with an acyclic olefin having from two to five carbon atoms per molecule wherein the olefin is supplied to the process in admixture with a paraffin having the same number of carbon atoms per molecule as the olefin; the olefin, the paraffin and benzene are contacted with an alkylation catalyst in a reaction zone to produce a reaction zone effluent stream comprising benzene, the alkylaromatic hydrocarbon and the paraffin; the reaction zone effluent stream is passed into a first fractionation zone which produces a first bottoms stream comprising benzene, the alkylaromatic hydrocarbon and the paraffin; and said first bottoms stream is passed into a second fractionation zone comprising a recycle fractionation column and wherein benzene is recovered for recycling to the reaction zone and the alkylaromatic hydrocarbon is removed in a bottoms stream; the improvement which comprises passing said first bottoms stream into a first recycle fractionation column, operated at a bottoms temperature of about 480° F. and pressure of about 385 psig effective to produce a net overhead stream consisting essentially of benzene and substantially all said paraffin in said first bottoms stream and a second bottoms stream comprising benzene and the alkylaromatic hydrocarbon; passing said second bottoms stream into a second recycle fractionation column operated at a bottoms temperature of about 480° F. and a lower pressure than said first recycle fractionation column, generating steam possessing a temperature of about 280° F. by the condensation of overhead vapors removed from said second recycle fractionation column, and withdrawing from said second recycle fractionation column a net overhead liquid stream consisting essentially of substantially pure benzene and a third bottoms stream comprising the alkylaromatic hydrocarbon; and recovering said alkylaromatic hydrocarbon from said third bottoms stream in a third fractionation column.

2. A process for the production of an alkylaromatic hydrocarbon which comprises the steps of:

(a) passing a feed stream which comprises benzene, an acyclic olefin having from two to five carbon atoms per molecule and a paraffin having the same number of carbon atoms per molecule as the olefin through an alkylation zone maintained at alkylation-promoting conditions and thereby forming an alkylation zone effluent stream comprising benzene, an alkylaromatic hydrocarbon and the paraffin;

(b) passing the alkylation zone effluent stream into a first fractionation column, and withdrawing from the first fractionation column an overhead stream comprising the paraffin and a first bottoms stream comprising benzene, the alkylaromatic hydrocarbon and the paraffin;

(c) passing said first bottoms stream into a second fractionation column maintained at a bottoms temperature of about 480° F. and a pressure of about 385 psig to produce and withdraw from said second fractionation column a first net overhead stream consisting essentially of benzene and substantially all said paraffin in said first bottoms stream and a second bottoms stream comprising benzene and the alkylaromatic hydrocarbon, said second bottom stream being substantially free of said paraffin;

(d) passing said second bottoms stream into a third fractionation column which is operated at a bottoms temperature of about 480° F. and a lower pressure than said second fractionation column to generate steam possessing a temperature of about 280° F. by condensing the overhead vapors of said third fractionation column, and withdrawing from said third fractionation column a second net overhead stream consisting essentially of benzene which is substantially free of said paraffin and a third bottoms stream comprising said alkylaromatic hydrocarbon;

(e) recovering said alkylaromatic hydrocarbon from said third bottoms stream in a fourth fractionation column operated at a lower pressure than said third fractionation column; and, (f) recycling at least a portion of said second net overhead substantially pure benzene stream to said alkylation zone.

3. The process of claim 2 wherein the paraffin is propane.

4. The process of claim 3 wherein the alkylation zone contains a solid phosphoric acid catalyst.

5. The process of claim 2 wherein at least a portion of the first net overhead stream is passed into the first fractionation column as reflux.

6. The process of claim 2 wherein the temperature in the bottom of the second and the third fractionation columns is maintained within 50° F. of the temperature in the bottom of the third fractionation column.

* * * * *